(12) United States Patent
Britten et al.

(10) Patent No.: US 7,842,791 B2
(45) Date of Patent: Nov. 30, 2010

(54) DISPERSIBLE PHARMACEUTICAL COMPOSITIONS

(76) Inventors: Nancy Jean Britten, 4750 Norfolk Cir., Portage, MI (US) 49024; Niki Ann Waldron, 2460 Wildemere, Kalamazoo, MI (US) 49009; John W. Burns, 812 4$^{th}$ Ave. #8, Antigo, WI (US) 54409

( * ) Notice: Subject to any disclaimer, the term of this patent is extended or adjusted under 35 U.S.C. 154(b) by 826 days.

(21) Appl. No.: 10/687,986

(22) Filed: Oct. 17, 2003

(65) Prior Publication Data

US 2004/0214752 A1 Oct. 28, 2004

Related U.S. Application Data

(60) Provisional application No. 60/434,985, filed on Dec. 19, 2002.

(51) Int. Cl.
*C07H 15/20* (2006.01)
*A23J 1/14* (2006.01)

(52) U.S. Cl. ..................... 536/13.1; 530/377
(58) Field of Classification Search .................. None
See application file for complete search history.

(56) References Cited

U.S. PATENT DOCUMENTS

| | | | |
|---|---|---|---|
| 3,135,658 A | 6/1964 | Hanus et al. | 167/53.2 |
| 3,144,386 A | 8/1964 | Brightenback | 167/53 |
| 3,347,743 A | 10/1967 | Reuter et al. | 167/53.2 |
| 3,531,481 A | 9/1970 | Pfeiffer | 260/243 |
| 3,636,194 A | 1/1972 | Parizeau | 424/115 |
| 4,006,138 A | 2/1977 | Yang | 260/243 |
| 4,011,312 A | 3/1977 | Reuter et al. | 424/78 |
| 4,073,920 A | 2/1978 | Dowrick | 424/271 |
| 4,104,470 A | 8/1978 | Cise et al. | 544/27 |
| 4,172,138 A | 10/1979 | Rhodes | 424/271 |
| 4,298,732 A | 11/1981 | Stables | 544/20 |
| 4,299,501 A * | 11/1981 | Patil et al. | 366/349 |
| 4,318,852 A | 3/1982 | Heitman et al. | 260/239.1 |
| 4,388,307 A | 6/1983 | Cavanak | 424/177 |
| 4,400,503 A | 8/1983 | Yang | 544/28 |
| 4,442,101 A | 4/1984 | Ichihashi et al. | 424/250 |
| 4,464,367 A | 8/1984 | Labeeuw et al. | 424/246 |
| 4,474,780 A | 10/1984 | Daugherty | 424/246 |
| 4,504,657 A | 3/1985 | Bouzard et al. | 544/30 |
| 4,555,404 A | 11/1985 | Nishihata et al. | 514/201 |
| 4,616,080 A | 10/1986 | Chou et al. | 540/225 |
| 4,624,948 A | 11/1986 | Dürckheimer | 514/206 |
| 4,692,519 A | 9/1987 | Naito et al. | 540/227 |
| 4,812,561 A | 3/1989 | Hamashima et al. | 540/222 |
| 4,820,833 A | 4/1989 | Crisp et al. | 540/220 |
| 4,877,782 A | 10/1989 | Cazers et al. | 514/186 |
| 4,898,938 A | 2/1990 | Marsili | 540/230 |
| 4,902,683 A * | 2/1990 | Amin et al. | 514/206 |
| 4,912,211 A | 3/1990 | Bonfanti | 540/222 |
| 4,912,212 A | 3/1990 | Ochiai et al. | 540/227 |
| 4,933,443 A | 6/1990 | Hamashima et al. | 540/222 |
| 4,937,330 A | 6/1990 | Sacks et al. | 540/227 |
| 4,973,684 A | 11/1990 | Ochiai et al. | 540/222 |
| 5,017,380 A | 5/1991 | Hamashima et al. | 424/454 |
| 5,064,815 A | 11/1991 | Szentmiklósi et al. | 514/31 |
| 5,079,007 A | 1/1992 | Putnam | 424/422 |
| 5,103,012 A | 4/1992 | Heymes et al. | 548/194 |
| 5,143,137 A | 9/1992 | West | 160/199 |
| 5,314,685 A | 5/1994 | Tyle et al. | 424/401 |
| 5,338,761 A * | 8/1994 | Nakajima et al. | 514/772 |
| 5,342,612 A | 8/1994 | Daley et al. | 424/85.1 |
| 5,614,491 A | 3/1997 | Walch et al. | 514/11 |
| 5,721,359 A | 2/1998 | Dunn et al. | 540/227 |
| 5,736,151 A | 4/1998 | Foster et al. | 424/423 |
| 6,054,136 A | 4/2000 | Farah et al. | 424/400 |
| 6,395,746 B1 | 5/2002 | Cagle et al. | 514/300 |
| 6,440,964 B1 | 8/2002 | Cagle et al. | 514/230.05 |
| 6,509,327 B1 | 1/2003 | Cagle et al. | 514/171 |
| 2001/0049366 A1 | 12/2001 | Singh et al. | 514/171 |
| 2002/0110561 A1 * | 8/2002 | Teagarden et al. | 424/147.1 |
| 2002/0142999 A1 | 10/2002 | Cagle et al. | 514/171 |

FOREIGN PATENT DOCUMENTS

| | | | |
|---|---|---|---|
| CA | 670254 | 9/1963 | 167/186 |
| CA | 2018794 | 5/2000 | |
| EP | 0 058 015 A2 | 8/1982 | |

(Continued)

OTHER PUBLICATIONS

[Retrieved from]"http://www.nlm.nih.gov/cgi/mesh/2008/MB_cgi?field=uid&term=C514708" 1 page, 2008 [Retrived on Oct. 21, 2008].*

(Continued)

*Primary Examiner*—Andrew D Kosar
*Assistant Examiner*—Satyanarayana R Gudibande
(74) *Attorney, Agent, or Firm*—John H. Engelmann; Lucy X. Yang

(57) ABSTRACT

A pharmaceutical composition is provided comprising a vehicle that comprises (a) an amphipathic oil that is water dispersible and ethanol insoluble, (b) microcrystalline wax, and (c) a pharmaceutically acceptable non-aqueous carrier; and having an antibacterial substance in an antibacterially effective amount stably dispersed in the vehicle. The composition is suitable for administration by intramammary infusion to a milk producing animal for treatment and/or prevention of mastitis or other diseases of the udder, as well as for otic administration for treatment and/or prevention of an ear infection.

1 Claim, No Drawings

FOREIGN PATENT DOCUMENTS

| | | |
|---|---|---|
| EP | 0 271 306 B2 | 6/1988 |
| EP | 0 222 712 B1 | 6/1990 |
| EP | 0 265 044 B1 | 1/1992 |
| EP | 0278 656 B1 | 6/1992 |
| EP | 0 592 348 B1 | 4/1994 |
| EP | 0 356 325 B1 | 5/1994 |
| EP | 0 797 988 A3 | 10/1997 |
| EP | 0 982 035 A1 | 3/2000 |
| EP | 1 004 294 A1 | 5/2000 |
| GB | 980282 | 1/1965 |
| GB | 1089523 | 11/1967 |
| GB | 1181527 | 2/1970 |
| GB | 1 370 699 | 10/1974 |
| GB | 1456349 | 11/1976 |
| GB | 1589917 | 5/1981 |
| GB | 2273441 | 6/1994 |
| GB | 2273443 | 6/1994 |
| GB | 2273655 | 6/1994 |
| WO | WO 87/03876 | 7/1987 |
| WO | WO 88/01504 | 3/1988 |
| WO | WO 95/31180 | 11/1995 |
| WO | WO 96/06598 | 3/1996 |
| WO | WO 96/39146 | 12/1996 |
| WO | WO 98/25621 | 6/1998 |
| WO | WO 99/56727 | 11/1999 |
| WO | WO 99/61025 | 12/1999 |
| WO | WO 00/48571 | 8/2000 |
| WO | WO 01/89495 A2 | 11/2001 |
| WO | WO 01/89496 A2 | 11/2001 |

OTHER PUBLICATIONS

Owens, et. al. "Determination of Milk and Mammary Tissue Concentrations of Ceftiofur After Intramammary and Intramuscular Therapy" Journal of Diary Science, vol. 73, No. 12, 1990, pp. 3449-3456.

Chemical Abstracts, vol. 84, 184895j, p. 308 (1976).

Chemical Abstracts, vol. 97, 38761q, p. 556 (1982).

Chemical Abstracts, vol. 110, 212490z, p. 719 (1989).

Gao, Zhi-Hui, Atul J. Shukla, James R. Johnson, and William R. Crowley, "*Controlled Release of a Contraceptive Steroid from Biodegradable and Injectable Gel Formulations: In Vitro Evaluation*", Pharmaceutical Research, vol. 12, No. 6, pp. 857-863, (1995).

Gao, Zhi-Hui, William R. Crowley, Atul J. Shukla, James R. Johnson, and James F. Reger, "*Controlled Release of Contraceptive Steroids from Biodegradable and Injectable Gel Formulations: In Vivo Evaluation*", Pharmaceutical Research, vol. 12, No. 6, pp. 864-868, (1995).

National Formulary, 19$^{th}$ ed. (NF 19), pp. 2536-2537 (Microcrystalline), Jan. 1, 2000.

Notice OL 0050/5$^{th}$ edition, Sep. 15, 2004.

Definition of Microcrystalline wax, available at http:/en.wikipedia.org/wiki/Microcrystalline_wax, Jul. 10, 2008.

Definition of Carnauba wax, available at http:/en.wikipedia.org/wiki/Carnauba_wax, Jul. 10, 2008.

Definition of Beeswax, available at http:/en.wikipedia.org/wiki/Beeswax, Jul. 10, 2008.

* cited by examiner

DISPERSIBLE PHARMACEUTICAL COMPOSITIONS

This application claims priority of U.S. provisional application Ser. No. 60/434,985 filed on Dec. 19, 2002.

FIELD OF THE INVENTION

The present invention relates to a stable pharmaceutical composition comprising an antibacterial agent, in particular to a composition that is readily dispersible in bodily fluids. The invention also relates to a process for preparing such a composition and to a method of treatment and/or prevention of diseases caused by bacterial infection in a fluid-containing organ such as an udder of a milk-producing animal or an ear, comprising administration of the composition to the fluid-containing organ.

BACKGROUND OF THE INVENTION

Mastitis is an inflammation of the mammary gland of milk producing animals, for example dairy cows, most often caused by bacterial infection. Bacteria enter through the teat canal of the animal and can cause acute, clinical, or sub-clinical mastitis. Over 135 organisms have been documented as causative pathogens for bovine mastitis. Three of the major groups of pathogens are gram-positive cocci, gram-negative bacilli, and gram-positive bacilli. Hygiene, environmental factors, and metabolic disturbances deriving from high milk yield combine to create conditions favorable to the onset of mastitis. An increased somatic cell count, associated with mastitis, is positively correlated with infection and negatively correlated with milk production. Frequently, an infected cow must be removed from the herd and dried up. Mastitis often affects a cow during its entire life unless the disease is properly treated, and in extreme cases an animal may become so severely infected that she dies. Infection rates average from 10% to 30% of the cows in a typical herd, with losses per cow ranging from $185 to $250 per cow per year. Bovine mastitis is the most economically costly disease to the dairy industry, with losses estimated at two billion dollars annually in the United States alone. The majority of these losses are due to reduced milk production.

Intramammary administration of compositions comprising an antibiotic for prevention and treatment of mastitis in milk producing animals is well known. Several compositions suitable for such administration are formulated in aqueous based vehicles.

For example, British Patent Application No. 2,273,655 discloses compositions for intramammary use comprising an insoluble antibiotic in an aqueous suspension for treatment of mastitis.

International Patent Publication No. WO 95/31180 discloses a composition comprising the antibiotic cloxacillin benzathine in an aqueous base, and additionally a teat seal composition, in injectors for intramammary application.

European Patent Application No. 0 797 988 discloses a veterinary composition in the form of an aqueous gel containing an antibacterial agent, useful for intramammary administration for prevention and treatment of mastitis.

The chemical stability of many antibiotics is, however, severely limited in aqueous based compositions. Hence, a number of oil based formulations for treatment and/or prevention of mastitis have also been developed.

British Patent Application No. 1,456,349 discloses a composition of an anti-mastitis medicament dispersed in a gelled vehicle comprising a mineral oil or non-drying, semi-drying, or drying vegetable oil or a mixture thereof, other than a mixture of drying and semi-drying vegetable oils, and from 0.5% to 5% by weight of a fatty acid ester derived from a saturated or unsaturated monocarboxylic acid having from 12 to 20 carbon atoms, and glycerin, propylene glycol, a mono- or dihydric alcohol having from 1 to 12 carbon atoms, or a polyethylene glycol having a molecular weight of 200 to 6000. Such a composition is said to provide short milkout times.

European Patent Application No. 0 058 015 discloses an intramammary formulation comprising isoxazolyl penicillin and rifampicin in an acceptable carrier. This formulation is said to substantially eliminate intracellular staphylococci.

U.S. Pat. No. 5,342,612 to Daley et al. describes a composition comprising a potentiating or safening amount of an aqueous surfactant in combination with a tumor necrosis factor, wherein the surfactant is sterol, n-dodecylglucosid, decanoyl n-methylglucamid, dodecyl B-D-maltosid or octanoyl n-methylglucamid. Such a composition is said to provide an efficacious treatment for mastitis with minimal milk discard.

U.S. Pat. No. 4,073,920 to Dowrick discloses an intramammary composition comprising a suspension of a semi-solid synthetic penicillin in an oily vehicle that comprises triglycerides or propylene glycol diesters of fatty acids containing 8-10 carbon atoms. Such a composition is said to provide short milkout times and good stability and shelf life.

U.S. Pat. No. 5,064,815 to Szentmiklosi et al. relates to a primycin-containing colloidal basic gel comprising 5-30% of primycin and 95-70% of N-methyl-2-pyrrolidone.

International Patent Publication No. WO 88/01504 discloses an intramammary infusion comprising a first dosage unit comprising a pharmaceutically acceptable vehicle and a substance active against mammary infection, and a second, optional, dosage unit of active substance, the particles of which are microencapsulated within a membrane capable of degrading.

International Patent Publication No. WO 87/03876 discloses a veterinary composition for treatment of mammary disorders and keratoconjunctivitis comprising benzathine cephalothin and a veterinarily acceptable carrier.

British Patent Application No. 2,273,443 discloses a composition for treating mastitis, comprising an antibacterial and a seal comprising a polyethylene gel.

British Patent Application No. 2,273,441 discloses a composition for treating mastitis, comprising an antibacterial and a seal comprising a gel base containing a heavy metal salt.

British Patent Application No. 1,089,523 discloses a composition comprising an antibiotic in a hydrophobic viscous or gel base, and comprising in addition at least 10% by weight of a solid, finely divided physiologically innocuous non-gelling water soluble compound of average particle size below 150 microns.

U.S. Pat. No. 4,011,312 to Reuter & Tsuk discloses a prolonged release dosage form for treatment of mastitis consisting of an antimicrobial agent dispersed in a matrix of low molecular weight polyesters of glycolic and lactic acids, and shaped as a cylindrical bougie for insertion into the teat canal.

British Patent No. 1,589,917 discloses a composition comprising a crystalline sodium salt of clavulanic acid methyl ether and a pharmaceutically acceptable carrier. High tissue levels of medicament are said to be produced after administration.

European Patent Application No. 0 271 306 discloses a method of treating mammary disorders comprising administering an antibacterial in the form of particles, at least 65% of which have a size in the range 0-5 microns, suspended in a hydrophobic oily vehicle which comprises an oil and a gelling agent. Prolonged release of medicament is said to be achieved.

U.S. Pat. No. 4,172,138 to Rhodes discloses an infusion of a limited solubility penicillin salt in a slow release base, optionally with neomycin.

U.S. Pat. No. 3,636,194 to Parizeau discloses a composition for treating mastitis by intramammary infusion, comprising an antibiotic, a vegetable oil, an alcohol-soluble fraction of natural lecithin phospholipid material for promoting dispersion of the oil in milk, the phospholipid being selected from the group consisting of phosphatidyl choline and phosphatidyl ethanolamine and mixtures thereof and present in amount of at least 0.25% in said oil. Such compositions are said to provide rapid dispersion into milk and short milkout times.

British Patent Application 1,181,527 discloses a composition for treating mastitis comprising an active substance and a pharmaceutically acceptable oil base, said composition containing phospholipid material consisting substantially entirely of alcohol-soluble material for promoting dispersion of the composition in milk.

European Patent Application No. 0 222 712 discloses a composition which contains one or more antimicrobial agents dispersed in an oil consisting of a mixture of triglycerides of palmitic and stearic acid together with polyoxyethylenated cetyl alcohol and stearyl alcohol, and held in an oily medium of mineral, vegetable, synthetic or mixed extraction. Such compositions are said to speed up release of the antimicrobial agent in the udder, enhancing its biological potential, and reducing milkout time.

A Labrafil product brochure (Notice OL 0050/5th edition) from Gattefossé Corporation contains an extract from a thesis by Valette (1957), discussing characteristics of Labrafil™ M-1944CS in the ear canal. The same thesis describes an experiment involving injecting Labrafil™ M-1944CS mixed with gentian violet into a cow teat. It was shown that Labrafil™ wetted the entire surface of the mammary parenchyma section and reached the retromammary ganglion.

Non-aqueous aerosol mastitis formulations are disclosed in the patents cited individually below.
U.S. Pat. No. 3,135,658.
U.S. Pat. No. 3,144,386.
U.S. Pat. No. 3,347,743.
Canadian Patent No. 670,254.
British Patent No. 980,282.

In addition, amphipathic oils that are dispersible in water have been utilized in preparation of a number of pharmaceutical compositions not specifically developed for intramammary treatment and/or prevention of mastitis.

European Patent Application No. 0 982 035 discloses an alcohol free transparent solution which comprises a cyclosporin in a hydrophilic carrier medium comprising propylene glycol, a transesterification product of a natural vegetable oil triglyceride and a polyalkylene polyol, a polyoxyethylene hydrogenated castor oil product and triacetin.

International Patent Publication No. WO 00/48571 discloses a spontaneously dispersible composition for oral administration comprising N-benzoyl-staurosporine, a surfactant selected from the group consisting of a polyoxyethylene castor oil, a polyoxyethylene alkyl ether and a polysorbate and a transesterified ethoxylated vegetable oil as a co-surfactant.

U.S. Pat. No. 5,314,685 to Tyle et al. discloses a method of making an anhydrous formulation by preparing an anhydrous hydrophilic phase comprising at least one hydrophilic vehicle which is solubilizing at least one lipophilic pharmaceutically active agent, preparing an oily phase comprising at least one oily component which is partially miscible with the at least one hydrophobic vehicle and combining the oily phase with the anhydrous hydrophilic phase to form the anhydrous formulation.

European Patent No. 0 356 325 discloses a pharmaceutical composition for oral, topical, or parenteral administration containing a sparingly water-soluble active agent in an amount as high as 25% and at least one glyceride gelled with at least one cellulose polymer.

International Patent Publication No. WO 96/06598 describes pharmaceutical compositions for aerosol delivery comprising a medicament, a non-chlorofluorocarbon propellant, and a polyglycolized glyceride or derivative thereof.

U.S. Pat. No. 5,614,491 relates to a liquid preparation for oral and parenteral administration comprising a cyclosporin, a polyoxyethylene glycol fatty acid monoester, and a monohydric and/or polyhydric alcohol(s).

International Patent Publication No. WO 99/61025 discloses microemulsion proconcentrates with a piperidine substance P antagonist.

U.S. Pat. No. 6,054,136 describes compositions capable of forming a microemulsion, comprising an active principle, a lipophilic phase consisting of a mixture of fatty acid esters and glycerides, a surfactant, a cosurfactant, and a hydrophilic phase.

International Patent Publication No. WO 99/56727 discloses self-emulsifying microemulsion or emulsion preconcentrate compositions containing a poorly water soluble active agent, an effective amount of a low HLB oil component, and a surfactant system consisting essentially of at least one surfactant having an HLB of about 10 to 20, wherein the composition contains minor amounts or is substantially free of a hydrophilic solvent system.

European Patent Application No. 1 004 294 discloses a substantially anhydrous pharmaceutical composition comprising a nitric oxide donating compound, a mucoadhesive compound, and an emulsifier capable of forming a microemulsion on addition of water.

European Patent Application No. 0 265 044 describes $(Nva)^2$-cyclosporin compositions for treatment of autoimmune diseases.

U.S. Pat. No. 4,388,307 to Cavanak discloses a pharmaceutical composition comprising an active monocyclic peptide and at least one of the following: a nonionic ester of a triglyceride and a polyalkylene polyol, a saturated fatty acid triglyceride, and a mono- or diglyceride having improved physical and absorption properties.

Two articles by Gao et al. (1995) in *Pharmaceutical Research* 12(6), 857-868, "Controlled release of a contraceptive steroid from biodegradable and injectable gel formulations: in vitro evaluation" and "Controlled release of a contraceptive steroid from biodegradable and injectable gel formulations: in vivo evaluation", describe preparation of gels containing levonorgestrel, Labrafil™ M-1944CS, and glyceryl palmitostearate.

Formulations comprising an antibacterial agent and an anti-inflammatory agent, said to be suitable for otic administration to treat otic conditions, are disclosed in the patents and publications cited individually below.
U.S. Patent Publication No. 2002/142999.
U.S. Pat. No. 6,395,746 to Cagle et al.
U.S. Pat. No. 6,440,964 to Cagle et al.
U.S. Pat. No. 6,509,327 to Cagle et al.
International Patent Application No. WO 01/89495.
International Patent Application No. WO 01/89496.
European Patent No. 0 592 348.

All of the above patents and articles are incorporated herein by reference.

The most commonly used packaging containers and delivery devices for compositions intended for intramammary administration to treat and/or prevent mastitis in milk producing animals as well as for compositions for otic administration to treat ear infections are constructed of oxygen permeable plastic materials, for example polyethylene, polypropylene, etc. and mixtures thereof. The use of oxygen permeable packaging containers and delivery devices for anti-mastitis formulations and for compositions for treatment and prevention of ear infections, poses serious problems for long term chemical and/or physical stability of compositions comprising an ingredient, for example an active medicament or an excipient, that is prone to oxidative degradation.

Although the references cited above disclose a number of compositions for treatment of mastitis and other disease conditions, none addresses the problem of providing extended chemical and/or physical stability of compositions packaged in oxygen permeable containers, where the composition comprises a pharmaceutically active substance that is prone to oxidative degradation. Despite the above teachings, there still exists a need in the art for pharmaceutical compositions having one or more of the following advantages over prior art compositions used in treatment and prevention of mastitis by intramammary infusion: (a) extended chemical and/or physical stability even when packaged in oxygen permeable containers and delivery devices, particularly where the composition comprises a pharmaceutically active substance that is prone to oxidative degradation, (b) efficacy against a wide variety of infectious organisms, (c) rapid dispersibility in milk and in udder fluids to achieve efficacious medicament levels at sites of infection, (d) short milkout times for lactating cows, (e) zero day slaughter meat withdrawal period, (f) short milk withholding times post calving after dry cow treatment, and (g) minimal to no irritation after administration.

SUMMARY OF THE INVENTION

Novel pharmaceutical compositions having some or all of the advantageous attributes described above have now been developed. Accordingly, there is provided a pharmaceutical composition comprising a vehicle that comprises (a) an amphipathic oil that is water dispersible and ethanol insoluble, (b) microcrystalline wax, and (c) a pharmaceutically acceptable non-aqueous carrier; said vehicle having stably dispersed therein an antibacterial substance in an antibacterially effective amount.

In one embodiment the antibacterial substance is prone to oxidative degradation, and the composition exhibits extended chemical and/or physical stability when packaged in an oxygen permeable container or delivery device. Such a composition can, for example, be administered by intramammary infusion for treatment and/or prevention of mastitis or other diseases of the udder in a milk-producing animal, and is efficacious against a wide variety of infectious organisms.

The novel anti-mastitis composition has a low interfacial tension in aqueous fluids, thereby increasing dispersibility of the composition in milk and udder fluids, as compared to a conventional oil based formulation. This results in rapid distribution of the composition throughout the udder and thereby allows the antibacterial substance to reach infected tissue quickly, providing an efficacious level of the antibacterial substance at a site of infection. The interfacial tension of a composition in an aqueous fluid determines the energy needed for dispersion and spreading of the composition in the fluid, as well as the energy necessary for a suspended particle in the composition to cross the oil/milk or oil/udder fluid interfacial boundary.

Preferably the composition is one that produces suitably short milkout times. Milkout time for a lactating cow is the period of time from administration of a mastitis treatment to resumption of production of saleable milk. Following administration of a composition, the concentration of active substance in milk must be reduced to a level acceptable to health organizations before the milk is deemed suitable for human consumption. A suitably short milkout time reduces monetary losses to a dairy farmer caused by a mastitis outbreak.

Preferably the composition is one that provides a low milk withholding time post calving after dry cow treatment, with no antibiotic residues in the offspring.

Preferably the composition is one that provides a zero day slaughter meat withdrawal period. This attribute is especially important since it allows a farmer to dispose of a treated cow at any time it is financially advantageous, rather than being required to keep and feed a cow for a specified amount of time after its mastitis treatment.

A composition of the invention can alternatively or in addition be useful for treatment and/or prevention of an infection of the ear, for which purpose it can be administered by infusion into the ear canal of a human, companion animal, horse, livestock, or the like. Such a composition is efficacious against a wide variety of infectious organisms.

Thus a pharmaceutical composition as described above is provided for treatment and/or prevention of an ear infection, the composition having a low interfacial tension in an aqueous fluid, thereby increasing the dispersibility of the composition in the waxy moist environment of an ear, as compared to a conventional composition. The resulting rapid distribution of the composition throughout mucous membranes and lipid containing wax of the ear canal allows the antibacterial substance to reach infected tissue quickly, providing an efficacious level of the antibacterial substance at the site of infection. Such a pharmaceutical composition also produces a protective coating for inflamed mucous membranes of the ear.

Preferably such a composition helps to dissolve wax deposits in the ear, thus permitting better penetration of the antibacterial substance.

Preferably a composition of the invention has improved physical stability when compared to conventional oil and aqueous compositions, for example by virtue of improved composition resuspendability. A composition of the invention has been shown to cause flocculation of certain drugs, thereby improving resuspendability and eliminating the problem of suspension caking and possible delivery of a subpotent or non-efficacious dose.

Preferably a composition of the invention produces minimal to no irritation after administration.

A process is provided for preparing a pharmaceutical composition of the invention. The process comprises mixing, in any suitable order, an amphipathic oil that is water dispersible and ethanol insoluble, microcrystalline wax, a pharmaceutically acceptable non-aqueous carrier, and an antibacterial substance to provide a composition having extended chemical and/or physical stability as described herein.

Also provided is a therapeutic method of treatment or prevention of a bacterial infection in a subject, the method comprising administration of a composition as described herein to a fluid-containing organ of the subject via a natural exterior orifice of the organ, wherein upon such administration the composition disperses in the fluid. For example, the organ can be an udder of a milk-producing animal, in which case administration is by infusion or injection via a teat canal.

Alternatively, the organ can be an ear, in which case administration is by infusion or injection via the external auditory meatus of the ear.

Accordingly, in one embodiment a method is provided for treatment and/or prevention of an infectious disease of an udder, for example mastitis, in a milk producing animal, the method comprising intramammary infusion of a composition as provided herein.

More particularly, a method is provided for effecting targeted delivery of an antibacterial substance to a site of mastitis infection in a milk producing animal, the method comprising intramammary administration of a composition as provided herein, for example by infusion or injection, to the udder of the animal.

In another embodiment a method is provided for treatment and/or prevention of an infectious disease of an ear in a subject, the method comprising infusion or injection of a composition as provided herein into the ear.

More particularly, a method is provided for effecting targeted delivery of an antibacterial substance to a site of an ear infection in a subject, the method comprising infusion or injection of a composition as provided herein into the ear of the subject.

The present invention provides solutions to several longstanding problems in the art and possesses one or more advantages over compositions of prior art. Other features, advantages and benefits of the invention will be apparent from the description that follows.

DETAILED DESCRIPTION OF THE INVENTION

The invention provides a pharmaceutical composition comprising a vehicle that comprises an amphipathic oil that is water dispersible and ethanol insoluble, microcrystalline wax, and a pharmaceutically acceptable non-aqueous carrier; said vehicle having stably dispersed therein an antibacterial substance in an antibacterially effective amount. The term "ethanol insoluble" means that the amphipathic oil is essentially insoluble in ethanol at 20° C.

In a particular embodiment of the invention the antibacterial substance is prone to oxidative degradation. According to this embodiment, the composition exhibits extended chemical and/or physical stability even when packaged in an oxygen permeable container or delivery device. The term "extended chemical and/or physical stability" herein means that a composition of the invention has greater chemical and/or physical stability than a reference composition comprising the same antibacterial substance at the same concentration. A "reference composition" in the present context means a composition lacking one or both of the amphipathic oil and the microcrystalline wax, but otherwise similar to the composition of the invention.

Oxygen permeable containers or delivery devices can be made of any suitable thermoplastic material including, but not limited to, polymers and copolymers of polystyrene, polyacrylonitrile, polyvinyl chloride, and particularly polyolefins. Polyolefins include, for example, polyethylene, polypropylene, polybutenes, polyisoprenes, polypentenes, copolymers thereof, and the like, and mixtures thereof.

Compositions for intramammary administration are commonly packaged in syringes that are provided with a cannula nozzle for insertion into the teat to allow extrusion directly into the mammary gland via the streak canal. Intramammary suspension formulations are generally prepared in thickened vehicles to prevent settling of drug particles into the cannula nozzle, which can cause nozzle plugging resulting in incomplete expulsion of the composition.

Cephalosporins are a class of antibacterial substance, many of which have a broad spectrum of activity against both gram positive and gram negative bacteria.

In an early effort to develop an intramammary suspension of the cephalosporin ceftiofur, 12.5 mg/ml ceftiofur hydrochloride was suspended in a thickened vehicle comprising 20 mg/ml glyceryl monostearate in peanut oil. Although clinically efficacious, the potency of this composition fell to below 90% of label after storage for less than 18 months at room temperature when packaged in polyethylene syringes. Oxidative degradation of ceftiofur hydrochloride was determined to be the primary cause of this potency decline. A room temperature shelf life wherein at least 90% of label potency is retained for a minimum of 24 months is desired for an intramammary suspension.

A number of ceftiofur hydrochloride suspension compositions were then prepared in a variety of thickened vehicles and packaged in oxygen permeable polyethylene syringes. Ceftiofur hydrochloride formulations at a concentration of 12.5 mg/ml were manufactured. All vehicles were based on cottonseed oil, with the following additional components:

(1) 50 mg/ml microcrystalline wax.
(2) 70 mg/ml microcrystalline wax+1.0 mg/ml propyl gallate.
(3) 100 mg/ml microcrystalline wax+50 mg/ml Labrafil™ M-1944CS.
(4) 40 mg/ml Gelucire™ 62/05+10 mg/ml Gelucire™ 33/01.
(5) 70 mg/ml Lexemul™ AR.
(6) 2.5 mg/ml Coagulan™ GP-1.
(7) 10 mg/ml microcrystalline wax+5 mg/ml Hydrofol Glycerides™ T 57L.
(8) 30 mg/ml Drewpol™ 10-10-S.
(9) 15 mg/ml beeswax blend.
(10) 60 mg/ml Drewpol™ 10-10-S.
(11) 10 mg/ml beeswax blend+50 mg/ml Labrafil™ M-1944CS.
(12) 100 mg/ml microcrystalline wax+1.0 mg/ml propyl gallate.
(13) 70 mg/ml microcrystalline wax+100 mg/ml Labrafil™ M-1944CS.
(14) 70 mg/ml microcrystalline wax+100 mg/ml Labrafil™ M-1944CS+0.2 mg/ml butylated hydroxytoluene.
(15) 70 mg/ml microcrystalline wax+50 mg/ml Labrafil™ M-1944CS+1.0 mg/ml propyl gallate.
(16) 70 mg/ml microcrystalline wax+50 mg/ml Labrafil™ M-1944CS+0.2 mg/ml butylated hydroxytoluene.
(17) 50 mg/ml microcrystalline wax+1.0 mg/ml propyl gallate.
(18) 100 mg/ml microcrystalline wax+100 mg/ml Labrafil™ M-1944CS+1.0 mg/ml propyl gallate.
(19) 100 mg/ml microcrystalline wax+100 mg/ml Labrafil™ M-1944CS+0.2 mg/ml butylated hydroxytoluene.
(20) 100 mg/ml microcrystalline wax+50 mg/ml Labrafil™ M-1944CS+1.0 mg/ml propyl gallate.
(21) 100 mg/ml microcrystalline wax+50 mg/ml Labrafil™ M-1944CS+0.2 mg/ml butylated hydroxytoluene.
(22) 50 mg/ml microcrystalline wax+100 mg/ml Labrafil™ M-1944CS+0.2 mg/ml butylated hydroxytoluene.

Labrafil™ M-1944CS is an amphipathic oil that is dispersible in water and is essentially insoluble in ethanol at 20° C. Gelucire™ 62/05 and Gelucire™ 33/01 are essentially inert excipients derived from natural hydrogenated food grade fats and oils. Lexemul™ AR is an acid stable cationic, self emulsifying glyceryl monostearate. "Beeswax blend" refers to a blend containing white beeswax, carnauba wax and candelilla wax. Coagulan™ GP-1 is N-acyl glutamic acid diamide, an amino acid gelatinization agent for oil. Drewpol™ is a modified glyceride.

Most surprisingly, it was discovered that after 24 months storage at room temperature in oxygen permeable polyethylene syringes, only those ceftiofur hydrochloride compositions comprising both Labrafil™ M-1944CS and microcrystalline wax provided formulations that maintained at least 90% of label potency. Estimated room temperature shelf lives for the ceftiofur hydrochloride formulations comprising both Labrafil™ M-1944CS and microcrystalline wax in cottonseed oil were 2.4 to 3.7 times greater than estimated room temperature shelf lives of comparable formulations which did not contain Labrafil™ M-1944CS. Additionally, while a ceftiofur hydrochloride composition comprising Labrafil™ M-1944CS and beeswax blend in cottonseed oil, stored at room temperature, had a potency of less than 90% after storage for 24 months in oxygen permeable polyethylene syringes at room temperature, a ceftiofur hydrochloride formulation of comparable viscosity comprising Labrafil™ M-1944CS and microcrystalline wax in cottonseed oil exhibited a potency of greater than 90% of label after 24 months in the same storage conditions.

Compositions comprising a cephalosporin, an amphipathic oil that is water dispersible and ethanol insoluble, microcrystalline wax, and a non-aqueous carrier, in addition to providing extended chemical and/or physical stability, also provide efficacy against a wide variety of infectious organisms, rapid dispersion of the composition in milk and in udder fluids to achieve efficacious medicament levels at the site of infection, short milkout times for lactating cows, a zero day slaughter meat withdrawal period, short milk withholding times post calving after dry cow treatment, and minimal to no irritation after administration.

Antibacterial substances applicable to the current invention include any such substances that are effective for treatment and/or prevention of mammary disorders and/or infections of the ear. Suitable antibacterial substances include, but are not limited to, beta-lactam antibacterials such as penicillins, synthetic penicillins, cephalosporins, macrolides (such as tylosin, tilmicosin, aivlosin, erythromycin, azithromycin, spiramycin, josamycin, kitasamycin, and the like), lincosamides (such as lincomycin, clindamycin, primycin, and the like), pleuromutilins (such as tiamulin, valnemulin, and the like), penam penicillins (such as benzyl penicillin, phenoxymethyl penicillin, coxacillin, nafcillin, methicillin, oxacillin, amoxycillin, temocillin, ticarcillin, and the like), polypeptides, penicillinase-stable penicillins, acylamino and caroxypenicillins (such as piperacillin, azlocillin, mezlocillin, carbenicillin, temocillin, ticarcillin, and the like), broader spectrum penicillins (such as streptomycin, neomycin, framycetin, genatamicin, apramycin, amikacin, spectinomycin, amoxycillin, ampicillin, and the like), polymixins (such as polymixin B, polymixin E, and the like), sulfonamides (such as sulfamethazine, sulfadiazine, sulfamethoxypyridazine, sulfatroxazole, and the like, alone or in combination with trimethoprim), chloramphenicol, thiamphenicol, florfenicol, tetracyclines and derivatives thereof (such as tetracycline, chlortetracycline, oxytetracycline, doxycycline, minocycline, and the like), quinolones, fluoroquinolones, tiamulin, ciprofloxacin, colistin, domeclocycline, mafenide, methacycline, norfloxacin, ofloxacin, pyrimethamine, silver sulfadiazine, sulfacetamide, sulfisoxazole, tobramycin, vanemulin, oxazolidinones (such as (S)-N-((3-(3-fluoro-4-(4-(hydroxyacetyl)-1-piperazinyl)phenyl)-2-oxo-5-oxazolidinyl) methyl)acetamide (eperezolid), (S)-N-((3-(3-fluoro-4-(4-(morpholinyl) phenyl)-2-oxo-5-oxazolidinyl)methyl)acetamide (linezolid), N-((5S)-3-(3-fluoro-4-(4-(2-fluoroethyl)-3-oxy-1-piperazinyl)phenyl-2-oxy-5-oxazolidinyl)methyl)acetamide, (S)-N-((3-(5-(3-pyridyl)thiophen-2-yl)-2-oxy-5-oxazolidinyl)methyl)acetamide, (S)-N-((3-(5-(4-pyridyl)pyrid-2-yl)-2-oxy-5-oxazolidinyl)methyl)acetamide hydrochloride, and the like), aminoglycosides and aminocyclitols, amphenicol, ansamycin, carbaphenem, cephamycin, vancomycin, monobactam, oxacephem, systemic antibacterials (such as 2,4-diaminopyrimidine), nitrofuran sulfones, marbofloxacin, and the like, and combinations thereof.

It should be understood that any reference herein to a particular drug compound includes tautomers, stereoisomers, enantiomers, salts, hydrates, and prodrugs of that compound and is not specific to any one solid state form of the drug.

Preferred antibacterial agents of the current invention are cephalosporins including, but not limited to, ceftiofur hydrochloride, ceftiofur crystalline free acid, ceftiofur sodium, other ceftiofur salts, cephalexin, cephradine, cefquinome, cephacetrile, cephalonium, cefuroxime, cefazidime, ceftoperazone, crystalline sodium cephemethcarboxylate, crystalline cephem heptahydrate, crystalline cephalosporin di- or tri-hydrate, cephadroxil monohydrate, cephazolin sodium monohydrate, cefiximine, ceftaxime, ceftizoxime, ceftriaxone, crystalline o-formylcefamandole, salts of 3-acetoxymethyl-7-(iminocetamido)-cephalosporanic acid derivatives, crystalline monohydrate of 7-(D-alpha-amino-alpha-(p-hydroxyphenyl)acetamino)-3-methyl-3-cephem-1-carboxylic acid, crystalline hydrochloride salt of syn-7-((2-amino-1-thiazoyl)(methoxyimino)acetyl)amino)-3-methyl-3-cephem-4-carboxylic acid, crystalline cephem acid addition salts, crystalline (pivaloyloxy)methyl 7-beta-(2-(2-amino-4-thiazoyl)acetamido)-3-(((1-(2-(dimethylamino)ethyl)-1H-tetraazol-5-yl)thio)methyl)-3-cephem-4-carboxylate, crystalline cephalexin, crystalline cephalexin monohydrate, crystalline 7-(D-2-naphthyglycylamino)-3-methyl-3-cephem-4-carboxylic acid tetrahydrate, and the like. Examples of cephalosporin antibiotic compounds are disclosed in the patents and publications listed below, each of which is individually incorporated herein by reference.

U.S. Pat. No. 3,531,481 to Pfeiffer.
U.S. Pat. No. 4,006,138 to Yang.
U.S. Pat. No. 4,104,470 to Cise & Osborne.
U.S. Pat. No. 4,298,732 to Stables.
U.S. Pat. No. 4,318,852 to Heitman et al.
U.S. Pat. No. 4,400,503 to Yang.
U.S. Pat. No. 4,442,101 to Ichihashi et al.
U.S. Pat. No. 4,464,367 to Labeeuw & Montpellier.
U.S. Pat. No. 4,474,780 to Daugherty.
U.S. Pat. No. 4,504,657 to Bouzard et al.
U.S. Pat. No. 4,555,404 to Nishihata et al.
U.S. Pat. No. 4,616,080 to Chou & Lakin.
U.S. Pat. No. 4,624,948 to Durckheimer.
U.S. Pat. No. 4,692,519 to Naito et al.
U.S. Pat. No. 4,812,561 to Hamashima et al.
U.S. Pat. No. 4,820,833 to Crisp et al.
U.S. Pat. No. 4,877,782 to Cazers & Koshy.
U.S. Pat. No. 4,898,938 to Marsili.
U.S. Pat. No. 4,902,683 to Amin & Campbell.
U.S. Pat. No. 4,912,211 to Bonfanti.
U.S. Pat. No. 4,912,212 to Ochiai et al.
U.S. Pat. No. 4,933,443 to Hamashima et al.
U.S. Pat. No. 4,937,330 to Sacks et al.
U.S. Pat. No. 4,973,684 to Ochiai et al.
U.S. Pat. No. 5,017,380 to Hamashima et al.
U.S. Pat. No. 5,079,007 to Putman.
U.S. Pat. No. 5,103,012 to Heymes & Lutz.
U.S. Pat. No. 5,143,137 to Cazers et al.

U.S. Pat. No. 5,721,359 to Dunn et al.
U.S. Pat. No. 5,736,151 to Foster & Kiefer.
European Patent No. 0 278 656.
Canadian Patent Application No. 2,018,794.
Chemical Abstracts 84:184895j (1976).
Chemical Abstracts 97:38761q (1982).
Chemical Abstracts 110:212490z (1989).

The most preferred cephalosporins for use according to the present invention are ceftiofur and pharmaceutically acceptable salts thereof.

Where the antibiotic is ceftiofur or a pharmaceutically acceptable salt thereof, a preferred concentration range in a composition of the invention is about 1 to about 1000 mg/ml, more preferably about 5 to about 750 mg/ml, and still more preferably about 10 to about 100 mg/ml. For antibacterials other than ceftiofur, suitable concentration ranges that are antibacterially equivalent can be determined by one of skill in the art based upon published data.

The term "amphipathic oil" is defined as a substance with a distinctly polar region and a distinctly non-polar region. Structurally these two regions of the amphipathic oil are sufficiently far apart that the unique properties of the two regions are distinctly separate.

Amphipathic oils applicable to the current invention include all amphipathic oils that are water dispersible and ethanol insoluble.

Preferred such amphipathic oils are polyglycolized glycerides prepared by an alcoholosis reaction of natural triglycerides with polyethylene glycols, and examples include, but are not limited to, the following Gattefossé oils or substantially equivalent oils from another manufacturer: Labrafil™ M-1944CS, Labrafil™ M-1966CS, Labrafil™ M-1969CS, Labrafil™ M-1980CS, Labrafil™ M-2125CS, Labrafil™ WL-2609BS, Labrafil™ ISO, and combinations thereof.

Still more preferred amphipathic oils are polyglycolized glycerides prepared as above, comprising a main fatty acid component of either oleic acid or linoleic acid, and examples include, but are not limited to, the following Gattefossé oils or substantially equivalent oils from another manufacturer: Labrafil™ M-1944CS, Labrafil™ M-1966CS, Labrafil™ M-1969CS, Labrafil™ M-1980CS, Labrafil™ M-2125CS, Labrafil™ WL-2609BS, and combinations thereof.

Still more preferred amphipathic oils are polyglycolized glycerides prepared as above, comprising a main fatty acid component of oleic acid, and examples include, but are not limited to, the following Gattefossé oils or substantially equivalent oils from another manufacturer: Labrafil™ M-1944CS, Labrafil™ M-1966CS, Labrafil™ M-1980CS, and combinations thereof.

The most preferred amphipathic oil is peglicol 5-oleate, for example Labrafil™ M-1944CS of Gattfossé Corporation.

A preferred concentration range for the amphipathic oil in a composition of the invention is about 0.01% to about 99% weight/volume, more preferably about 1% to about 80% weight/volume, and still more preferably about 3% to about 25% weight/volume.

Microcrystalline wax is as defined for example in *Handbook of Pharmaceutical Excipients*, 3rd ed. or in *National Formulary*, 19th ed. (NF 19) and can be obtained from a number of manufacturers including Witco Corporation.

A preferred concentration range for microcrystalline wax in a composition of the invention is about 0.01% to about 50% weight/volume, more preferably about 1% to about 40% weight/volume, and still more preferably about 3% to about 15% weight/volume.

Pharmaceutically acceptable non-aqueous carriers of the invention can be fully saturated, or partially or fully unsaturated. Examples of non-aqueous carriers include, but are not limited to, vegetable oils (such as cottonseed oil, corn oil, sesame oil, soybean oil, olive oil, fractionated coconut oils, peanut oil, sunflower oil, safflower oil, almond oil, avocado oil, palm oil, palm kernel oil, babassu oil, beechnut oil, linseed oil, rape oil, and the like), mineral oils, synthetic oils, and combinations thereof. Examples of fully saturated non-aqueous carriers include, but are not limited to, esters of medium to large chain fatty acids (such as fatty acid triglycerides with a chain length of about $C_6$ to about $C_{24}$). Mixtures of fatty acids are split from the natural oil (for example coconut oil palm kernel oil, babassu oil, or the like) and are refined. In some embodiments, about $C_8$ to about $C_{12}$ fatty acid medium chain triglycerides are useful. An illustrative saturated non-aqueous carrier comprises capric acid (about 20% to about 45% by weight of the carrier) and caprylic acid (about 45% to about 80% by weight of the carrier). Other fully saturated non-aqueous carriers include, but are not limited to, saturated coconut oil (which typically includes a mixture of lauric, myristic, palmitic, capric and capric acids), including those sold under the Miglyol™ trademark from Huls and bearing trade designations 810, 812, 829, and 840). Also noted are the NeoBee™ products sold by Drew Chemicals. Isopropyl myristate is another example of a non-aqueous carrier useful in compositions of the invention. Examples of synthetic oils include triglycerides, and propylene glycol diesters of saturated or unsaturated fatty acids having from 6 to 24 carbon atoms such as, for example hexanoic acid, octanoic (caprylic), nonanoic (pelargonic), decanoic (capric), undecanoic, lauric, tridecanoic, tetradecanoic (myristic), pentadecanoic, hexadecanoic (palmitic), heptadecanoic, octadecanoic (stearic), nonadecanoic, heptadecanoic, eicosanoic, heneicosanoic, docosanoic, and lignoceric acids, and the like. Examples of unsaturated carboxylic acids include oleic, linoleic, and linolenic acids, and the like. It is understood that the non-aqueous carrier can comprise the mono-, di-, and triglyceryl esters of fatty acids or mixed glycerides and/or propylene glycol diesters wherein at least one molecule of glycerol has been esterified with fatty acids of varying carbon atom length. A non-limiting example of a "non-oil" of the present invention is polyethylene glycol.

Preferred non-aqueous carriers are selected from the group consisting of cottonseed oil, corn oil, peanut oil, sesame oil, soybean oil, olive oil, sunflower oil, safflower oil, almond oil, avocado oil, palm oil, palm kernel oil, babassu oil, beechnut oil, linseed oil, rape oil, and fractionated coconut oil.

The most preferred non-aqueous carrier is cottonseed oil. By way of example cottonseed oil is available in a preparation of 70% unsaturated fatty acids from Sigma Chemical Co.

A preferred concentration range for the non-aqueous carrier in a composition of the invention is about 0.5% to about 99% weight/volume, more preferably about 10% to about 95% weight/volume, and still more preferably about 40% to about 90% weight/volume.

A composition of the invention can be admixed with any conventional pharmaceutical additive which does not deleteriously react with the composition, including, but not limited to, antioxidants, preservatives, stabilizers, wetting agents, lubricants, emulsifiers, salts for influencing osmotic pressure, coloring agents, alcohols, buffering agents, other conventional pharmaceutical additives, and combinations thereof. Examples include, but are not limited to, tocopherols, ascorbyl palmitate, butyl hydroxyanisole, butyl hydroxytoluene, benzoic acid, benzoic acid derivatives, ethylenediamine, sodium bisulfite, sulfur dioxide, maleic acid, propyl gallate, magnesium stearate, talc, silicic acid, carbohydrates (such as lactose, amylose, and starch), and combinations thereof.

Methods of administration of a composition of the invention are described herein as involving "infusion" or an "infusing" step. The terms "infusion" and "infusing" herein refer to a process of delivering a liquid composition directly into a fluid-containing organ, and encompass injection, for example using a syringe, that is completed within a very short space of time as well as more prolonged delivery.

A composition of the invention can be administered for treatment or prevention of mastitis by inserting the cannula nozzle of a mastitis syringe into the external orifice of the streak canal of an udder of a milk producing animal and infusing the composition into the udder.

A composition of the invention can be administered for treatment or prevention of an ear infection by inserting the nozzle of an ear syringe, otic drop dispenser, or other appropriate otic delivery device into the external auditory canal of the ear of a subject and infusing the composition into the ear.

It will be appreciated that the preferred amounts of compositions to be administered in a specific case will vary according to the specific composition being utilized, the mode of application, the particular situs and organism being treated, and other factors. Dosages for a given purpose can be determined using conventional considerations, for example, by customary comparison of the differential activities of the subject compositions and of a known agent, e.g., by means of an appropriate conventional pharmaceutical protocol.

An illustrative suspension of the invention containing as the antibacterial substance ceftiofur hydrochloride has the following composition:

| | |
|---|---|
| antibacterial substance | 1–1000 mg/ml |
| Labrafil ™ M-1944CS | 0.01–99% |
| microcrystalline wax | 0.01–50% |
| cottonseed oil | 0.5–99% |

(all percentages are weight/volume).

EXAMPLES

The following examples illustrate aspects of the present invention but should not be construed as limitations.

Example 1

A suspension to be administered by intramammary infusion for treatment and/or prevention of lactating cow mastitis was prepared having the following composition:

| | |
|---|---|
| ceftiofur hydrochloride (micronized) | 12.5 mg/ml |
| Labrafil ™ M-1944CS | 50 mg/ml |
| microcrystalline wax NF | 70 mg/ml |
| cottonseed oil NF | q.s. |

The microcrystalline wax and approximately 27% of the total amount of the cottonseed oil were heated to 85-98° C. with mixing, in a kettle. The balance of the cottonseed oil was heated to 85-98° C. with mixing, in a manufacturing tank. After the microcrystalline wax was completely melted the microcrystalline wax/cottonseed oil mixture in the kettle was transferred to the manufacturing tank containing cottonseed oil and mixed thoroughly. The resulting mixture was cooled to 38-45° C. and the Labrafil™ M-1944CS was added to the manufacturing tank with mixing to form a vehicle. The ceftiofur hydrochloride was then added to the vehicle and the resulting composition was mixed to form a uniform suspension. The suspension was screened and filled into 12 ml high density polyethylene mastitis syringes. The packaged product was terminally sterilized by gamma irradiation at a dose of 25-40 kGy.

The interfacial tension of the above suspension was determined using the drop volume technique by comparison with that of a reference suspension prepared with 70 mg/ml microcrystalline wax in cottonseed oil but without Labrafil™ M-1944CS. The interfacial tension of the suspension containing both Labrafil™ M-1944Cs and microcrystalline wax in cottonseed oil was 3.4 times lower than that of the reference suspension.

Example 2

A suspension to be administered by intramammary infusion for treatment and/or prevention of lactating cow mastitis was prepared having the following composition:

| | |
|---|---|
| ceftiofur hydrochloride (micronized) | 12.5 mg/ml |
| Labrafil ™ M-1944CS | 50 mg/ml |
| microcrystalline wax NF | 100 mg/ml |
| cottonseed oil NF | q.s. |

The microcrystalline wax and cottonseed oil were heated to 85-98° C. with mixing, in a manufacturing tank. After the microcrystalline wax was completely melted the mixture was cooled to 38-45° C. and the Labrafil™ M-1944CS was added to the manufacturing tank with mixing. Ceftiofur hydrochloride was then added to the resulting vehicle and mixed to form a uniform suspension. The suspension was screened and filled into 12 ml high density polyethylene mastitis syringes. The packaged product was terminally sterilized by gamma irradiation at a dose of 25-40 kGy.

The interfacial tension of the above suspension was determined using the drop volume technique by comparison with that of a reference suspension prepared with 100 mg/ml microcrystalline wax in cottonseed oil but without Labrafil™ M-1944CS. The interfacial tension of the suspension containing both Labrafil™ M-1944Cs and microcrystalline wax in cottonseed oil was 4.0 times lower than that of the reference suspension.

Example 3

A suspension to be administered by intramammary infusion for treatment and/or prevention of lactating cow mastitis was prepared having the following composition:

| | |
|---|---|
| ceftiofur hydrochloride (micronized) | 12.5 mg/ml |
| Labrafil ™ M-1944CS | 200 mg/ml |
| microcrystalline wax NF | 100 mg/ml |
| cottonseed oil NF | q.s. |

The microcrystalline wax and cottonseed oil were heated to 85-98° C. with mixing, in a manufacturing tank. After the microcrystalline wax was completely melted the mixture was cooled to 38-45° C. and Labrafil™ M-1944CS was added to the manufacturing tank with mixing. The ceftiofur hydrochloride was then added to the resulting vehicle and mixed to form a uniform suspension. The suspension was screened and filled into 12 ml high density polyethylene mastitis syringes.

The packaged product was terminally sterilized by gamma irradiation at a dose of 25-40 kGy.

The interfacial tension of the above suspension was determined using the drop volume technique by comparison with that of a reference suspension prepared with 100 mg/ml microcrystalline wax in cottonseed oil but without Labrafil™ M-1944CS. The interfacial tension of the suspension containing both Labrafil™ M-1944CS and microcrystalline wax in cottonseed oil was more than 28 times lower than that of the reference suspension.

Example 4

A suspension to be administered by intramammary infusion for treatment and/or prevention of lactating and dry cow mastitis is prepared having the following composition:

| | |
|---|---|
| ceftiofur crystalline free acid (micronized) | 25.0 mg/ml |
| Labrafil ™ M-1966CS | 100 mg/ml |
| microcrystalline wax NF | 50 mg/ml |
| corn oil NF | q.s. |

The microcrystalline wax and the corn oil are heated to 85-98° C. with mixing, in a manufacturing tank. After the microcrystalline wax is completely melted, the mixture is cooled to 30-45° C. and the Labrafil™ M-1966CS is added to the manufacturing tank with mixing. The ceftiofur crystalline free acid is added to the vehicle and mixed to form a uniform suspension. The suspension is screened and filled into 12 ml high density polyethylene mastitis syringes. The packaged product is terminally sterilized by gamma irradiation at a dose of 25-40 kGy.

Example 5

A suspension to be administered by otic infusion for treatment and/or prevention of canine otitis externa is prepared having the following composition:

| | |
|---|---|
| ceftiofur hydrochloride (micronized) | 25 mg/ml |
| Labrafil ™ M-1980CS | 500 mg/ml |
| microcrystalline wax NF | 1.0 mg/ml |
| propyl gallate | 1.0 mg/ml |
| mineral oil | q.s. |

The microcrystalline wax and approximately 27% of the total amount of the mineral oil are heated to 85-98° C. with mixing, in a kettle. The balance of the mineral oil is heated to 85-98° C. with mixing, in a manufacturing tank. After the microcrystalline wax is completely melted, the microcrystalline wax/mineral oil mixture in the kettle is transferred to the manufacturing tank containing mineral oil and mixed thoroughly. The resulting mixture is cooled to 38-45° C. and the Labrafil™ M-1980CS is added to the manufacturing tank with mixing. The ceftiofur hydrochloride is then added to the resulting vehicle and mixed to form a uniform suspension. The suspension is screened and filled into 20 ml polypropylene containers.

Example 6

A suspension to be administered by intramammary infusion for treatment and/or prevention of dry cow mastitis was prepared having the following composition:

| | |
|---|---|
| ceftiofur hydrochloride (micronized) | 50 mg/ml |
| Labrafil ™ M-1944CS | 50 mg/ml |
| microcrystalline wax NF | 70 mg/ml |
| cottonseed oil NF | q.s. |

The microcrystalline wax and approximately 27% of the total amount of the cottonseed oil were heated to 85-98° C. with mixing, in a kettle. The balance of the cottonseed oil was heated to 85-98° C. with mixing, in a manufacturing tank. After the microcrystalline wax was completely melted the microcrystalline wax/cottonseed oil mixture in the kettle was transferred to the manufacturing tank containing cottonseed oil and mixed thoroughly. The resulting mixture was cooled to 38-45° C. and the Labrafil™ M-1944CS was added to the manufacturing tank with mixing. The ceftiofur hydrochloride was then added to the resulting vehicle and mixed to form a uniform suspension. The suspension was screened and filled into 12 ml high density polyethylene mastitis syringes. The packaged product was terminally sterilized by gamma irradiation at a dose of 25-40 kGy.

Example 7

A suspension to be administered by intramammary infusion for treatment and/or prevention of lactating cow mastitis is prepared having the following composition:

| | |
|---|---|
| ceftiofur sodium (micronized) | 20 mg/ml |
| Labrafil ™ WL-2609BS | 75 mg/ml |
| microcrystalline wax NF | 100 mg/ml |
| Miglyol ™ 812 | q.s. |

The microcrystalline wax and approximately 30% of the total amount of the Miglyol™ 812 are heated to 85-98° C. with mixing, in a kettle. The balance of the Miglyol™ 812 is heated to 85-98° C. with mixing, in a manufacturing tank. After the microcrystalline wax is completely melted the microcrystalline wax/Miglyol™ 812 mixture in the kettle is transferred to the manufacturing tank containing the Miglyol™ 812 and mixed thoroughly. The resulting mixture is cooled to 38-45° C. and the Labrafil™ WL-2609BS is added to the manufacturing tank with mixing. The ceftiofur sodium is added to the resulting vehicle and mixed to form a uniform suspension. The suspension is screened and filled into 12 ml high density polyethylene mastitis syringes. The packaged product is terminally sterilized by gamma irradiation at a dose of 25-40 kGy.

The invention having been described in detail and by reference to the preferred embodiments thereof, it will be apparent that modifications and variations are possible without departing from the scope of the appended claims.

What is claimed is:

1. A rapid distribution pharmaceutical composition consisting of peglicol-5-oleate, microcrystalline wax, cottonseed oil, and ceftiofur hydrochloride.

* * * * *